United States Patent [19]

Dobson

[11] Patent Number: 4,484,572
[45] Date of Patent: Nov. 27, 1984

[54] POSITION SECURING DEVICE

[76] Inventor: James L. Dobson, 1268 Lee Ann Dr., Decatur, Ga. 30035

[21] Appl. No.: 468,353

[22] Filed: Feb. 22, 1983

[51] Int. Cl.³ .............................................. A61F 5/04
[52] U.S. Cl. .................................................. 128/134
[58] Field of Search ..................... 128/134, 133, 94; 269/328

[56] References Cited

U.S. PATENT DOCUMENTS 2,851,033  9/1958  Posey .................................... 128/134
4,223,670  9/1980  Cramer .................................. 128/134

Primary Examiner—John D. Yasko
Attorney, Agent, or Firm—James B. Middleton

[57] ABSTRACT

A position retaining device for allowing a person to maintain the prenatal position while sleeping. The retaining device has straps passing over the shoulders, and a horizontal strap holding the shoulder straps on the shoulders. Extensions from the shoulder straps provide a pair of sling members in the front, the sling members being such as to pass around the thighs to hold the legs up, somewhat in the prenatal position. A bow knot, for example, can be used to secure the sling members for ready release.

5 Claims, 3 Drawing Figures

U.S. Patent    Nov. 27, 1984    4,484,572

POSITION SECURING DEVICE

FIELD OF THE INVENTION

This invention relates generally to restraining means, and is more particularly concerned with an apparatus for maintaining a given position while sleeping.

BACKGROUND OF THE INVENTION

It is well known that numerous people have some problems with the lower, or lumbar, region of their back. Due to the natural curvature of a person's backbone, and the fact that the lumbar area of the backbone necessarily carries the weight of the entire upper torso, tall people are especially given to the lower back problems. It has been noted that there will be some amelioration of the condition if one sleeps with the knees drawn up, somewhat in the prenatal position.

Though the benefit of sleeping in the prenatal position has long been recognized, there has been no reasonable means for a person to assure that he will maintain that position throughout the sleeping period. While various body restraints are well known in the art, it should be realized that a device intended to keep a person voluntarily in the prenatal position must be sufficiently comfortable to allow the person to sleep in a relaxed condition, and to allow the person to release the device quite easily when desired.

SUMMARY OF THE INVENTION

The present invention provides an admirable solution to the above stated problems by providing a comfortable and readily releasable position securing device. The device includes strap means carried by a person's upper body portion, and separable sling means depending from said strap means for selectively encircling a person's legs. In one embodiment of the invention, the strap means takes the form of a vest-like structure, with the sling means formed integrally with the vest-like structure. The sling means may be separable by means of an ordinary bow knot; or, other fastening means such as hook and teasel or the like may be utilized. The vest-like arrangement therefore provides comfort for the wearer, the apparatus being formed of material that is soft, and wide enough to distribute the forces over a generous portion of the person's body. Similarly, the sling means is wide enough and soft enough to encircle one's legs comfortably.

BRIEF DESCRIPTION OF THE DRAWINGS

These and other features and advantages of the present invention will become apparent from consideration of the following specification when taken in conjunction with the accompanying drawings in which.

DESCRIPTION OF AN EMBODIMENT OF THE INVENTION

Figure 1:
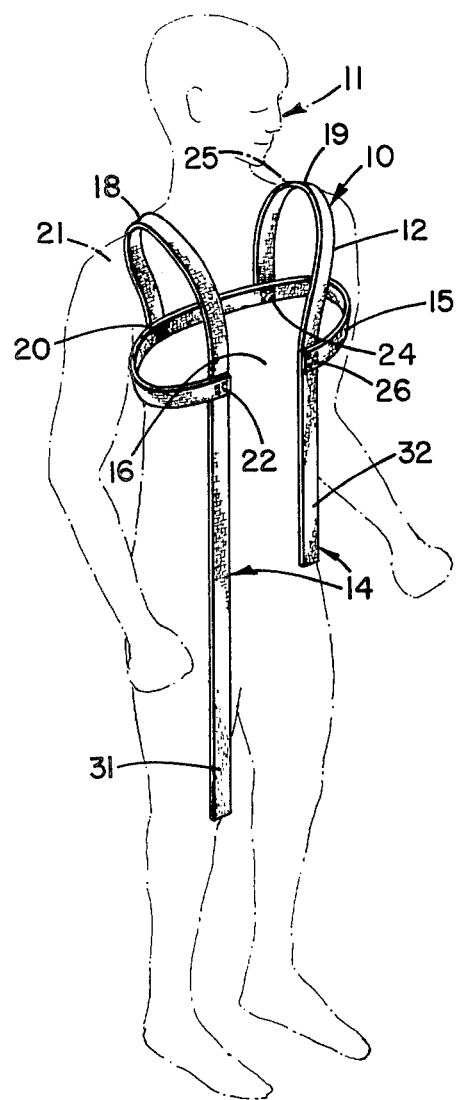
FIG. 1 is a perspective view showing a device made in accordance with the present invention, with a person wearing the device shown in phantom.

Referring now more particularly to the drawings, and to that embodiment of the invention here presented by way of illustration, FIG. 1 shows the position securing device generally indicated at 10 as worn by a person generally indicated in phantom at 11. It will be seen that the securing device 10 comprises the strap means 12 carried by the upper portion of the body 11, and separable sling means 14 depending from the strap means 12. In FIG. 1, the sling means 14 is shown separated and including parts 31 and 32.

The strap means 12 is a generally vest-like structure including an encircling strap 15 that extends around the body; however, it will be noted that there is a gap 16 in the front.

There are two shoulder straps 18 and 19. It will be seen that the shoulder strap 18 is fixed to the encircling strap 15, as at 20. The shoulder strap 18 can then pass over the shoulder 21 of the person 11, and down to the end 22 of the body encircling strap 15.

Similarly, the shoulder strap 19 is fixed to the body encircling strap 15 in the rear, as at 24. The shoulder strap 19 then extends over the shoulder 25 and down, to be attached to the end 26 of the body encircling strap 15.

It will therefore be seen that the strap means is made very much as a vest, the device being supported by the shoulders 21 and 25 of the person 11. The body encircling strap 15 is complete at the back of the person but is provided with the opening 16 at the front of the person so the ends 22 and 26 of the body encircling strap 15 will not meet.

The separable sling means 14 can conveniently be provided by integral extensions of the shoulder straps 18 and 19. It will be understood that the strap material of the shoulder strap 18 can be fixed to the end 22 of the body encircling strap 15, and continue down to the desired length. Similarly, the material of the shoulder strap 19 can be fixed to the body encircling strap 15 at its end 26, and the material of the strap 19 can continue down to the desired length.

While the device shown in the drawings includes the opening 16, it will readily be understood by those skilled in the art that the body encircling strap 15 may be completely closed, or closable. If the strap 15 is permanently closed, it will be understood that the device must be made in different sizes to accommodate different body sizes, though of course the front closure member could be adjustable by means of hook and teasel material, buttons or the like. Furthermore, it will be understood that some provision must be made for women to prevent discomfort. It will be observed in FIGS. 1 and 2 of the drawings that the body encircling strap 15 is located generally in the bust area. For this reason, the opening 16 is preferable for maximum comfort for both men and women, yielding the additional advantage of allowing one size of the device to fit a wide variety of people.

Figure 2:
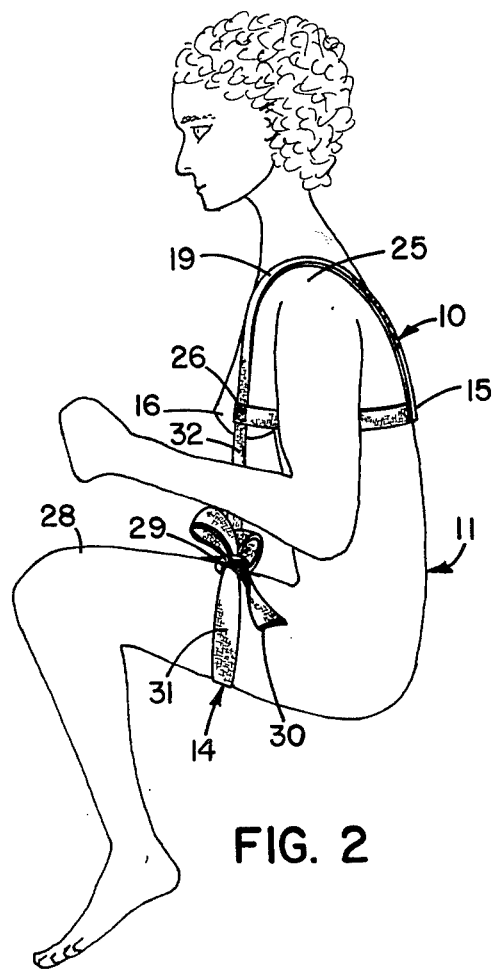
FIG. 2 is a side elevational view of a person utilizing the apparatus shown in FIG. 1 with the person held generally in the prenatal position; and, FIG. 3 is a front elevational view of the device shown in FIG. 1.

Looking specifically now at FIG. 2 of the drawings, it will be seen that the person 11 has the strap means 12 in position on the upper body portion, and the sling means 14 is fastened to hold the legs 28 up. In FIG. 2, it will be seen that the front portions of the body encircling strap 15 will move away from the body to follow the dictates of the sling means 14.

It will also be seen in FIG. 2 of the drawings that the sling means 14 is held by means of a bow knot 29. It should be noted that the loose end 30 is readily accessible to allow the sling means to be released. It will be realized that, if a person lying in bed using the device of the present invention becomes cramped, or has other difficulties, the sling means 14 should be quickly released. The use of the bow knot 29 provides a very simple mean for releasing the sling means 14 when desired.

It will be noticed that the person 11 in FIG. 2 of the drawings is utilizing the sling means 14 to hold the legs 28 in a position something close to a sitting position. It will be recognized by those skilled in the art that the length of the sling means 14 is readily changeable to pull the legs 28 up higher to more closely approximate the prenatal position; or, the sling means 14 may be lengthened to allow the legs 28 to be lowered. The device is therefore quite variable depending on personal preferences.

Figure 3:
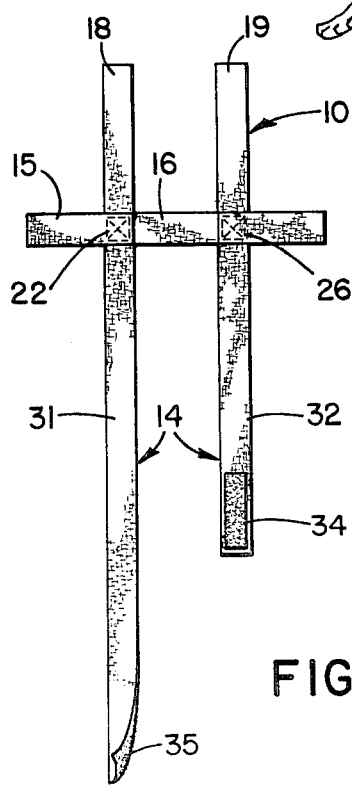

Looking now at FIG. 3 of the drawings, it will be seen that the device 10 is preferably formed of strap material, and the strap material should preferably be soft and yielding, such as knit fabric or the like. It has been found that strap material having approximately a 2-inch width works quite well, giving sufficient width for comfort without being so wide as to cause difficulty in manipulating the device.

The apparatus is readily manufactured by cutting only three lengths of material, these three lengths being the body encircling strap 15, the shoulder strap 18 with the sling portion 31, and finally the shoulder strap 19 with sling portion 32. Each of these straps can be sewn or otherwise affixed to the body encircling strap 15 to provide the attachments 20 and 24, and can again be fixed to the body encircling strap 15 at the ends 22 and 26. The sling portions 31 and 32 can extend downwardly to the desired length, and preferably rather long so one size will accommodate a wide range of sizes of people.

While the use of a knot 29 has been discussed in conjunction with the device as shown in FIG. 2, it will also be seen in FIG. 3 of the drawings that hook and teasel may be used to hold the portions 31 and 32 of the sling means 14 together. As here shown, the hook member 34 is carried by the sling portions 32, and the teasel 35 is carried by the sling portion 31. While this is obviously reversable, it is preferable that the teasel 35 be the one more likely to contact the person's skin since the hook material 34 would tend to be uncomfortable.

It will therefore be seen that the present invention provides a vest-like structure that is very simple to don, and the open front will allow a single size to fit a wide variety of people. The sling means extending from the vest-like structure can be selectively fixed around a person's legs to hold the legs up in the desired position, while being readily releasable so the person can straighten out, for example to rise in the morning without assistance.

It will of course be understood by those skilled in the art that the particular embodiment of the invention here presented is by way of illustration only, and is meant to be in no way restrictive; therefore, numerous changes and modifications may be made, and the full use of equivalents resorted to, without departing from the spirit or scope of the invention as defined in the appended claims.

I claim:

1. A position retaining device, for voluntary use by a person wishing to remain generally in the prenatal position, said retaining device comprising a vest portion for being received over the upper body of said person, said vest portion including a first shoulder strap and a second shoulder strap, each said shoulder strap passing over one shoulder of said person, and a body encircling strap generally encircling the body of said person approximately in the chest area of said person, said shoulder straps being fixed to said body encircling strap at the back of said person, said first shoulder strap being fixed at a first back point and said second shoulder strap being fixed at a second back point, said first back point and said second back point being spaced apart along said body encircling strap, said shoulder straps being fixed to said body encircling strap at the front of said person, said first shoulder strap being fixed at a first front point and said second shoulder strap being fixed at a second front point, said first front point and said second front point being arranged for relative motion therebetween, said retaining device further including separable sling means depending from the front of said vest portion, said sling means including a first sling strap depending from said body encircling strap, said first sling strap being fixed to said body encircling strap generally at said first front point, a second sling strap depending from said body encircling strap, said second sling strap being fixed to said body encircling strap generally at said second front point, and fastening means for selectively fastening said sling means around the legs of said person while said person is generally in the prenatal position, said fastening means being readily releasable by said person.

2. A device as claimed in claim 1, said first sling strap and said second sling strap having a total length sufficient to encircle the thighs of said person when said person is generally in the prenatal position.

3. A device as claimed in claim 2, said body encircling strap defining an opening between said first front point and said second front point.

4. A device as claimed in claim 3, said fastening means comprising a bow knot for quick release of said fastening means, said first sling strap having sufficient length to pass around the thighs of the person and locate said bow knot at one side of said person.

5. A device as claimed in claim 3, said fastening means comprising hook and teasel for quick release of said fastening means, said first sling strap having sufficient length to pass around the thighs of the person and locate said hook and teasel at one side of said person.

* * * * *